(12) United States Patent
Kakuo et al.

(10) Patent No.: US 7,147,877 B2
(45) Date of Patent: Dec. 12, 2006

(54) METHOD FOR TREATING LESIONS CAUSED BY ESTROGEN DEFICIENCY WITH EXTRACT OF CUCUMBER

(75) Inventors: Shingo Kakuo, Tochigi (JP); Shigeru Moriwaki, Tochigi (JP); Atsushi Ohuchi, Tochigi (JP); Hiroshi Kusuoku, Tochigi (JP)

(73) Assignee: Kao Corporation, Tokyo (JP)

( * ) Notice: Subject to any disclaimer, the term of this patent is extended or adjusted under 35 U.S.C. 154(b) by 85 days.

(21) Appl. No.: 10/725,451

(22) Filed: Dec. 3, 2003

(65) Prior Publication Data
US 2004/0265399 A1    Dec. 30, 2004

(30) Foreign Application Priority Data
Dec. 6, 2002  (JP) ............................ 2002-355578

(51) Int. Cl.
*A61K 36/42*    (2006.01)
(52) U.S. Cl. ...................................... 424/758; 424/725
(58) Field of Classification Search ................ 424/725, 424/758
See application file for complete search history.

(56) References Cited

U.S. PATENT DOCUMENTS 1,687,154 A * 10/1928 Bolton ....................... 426/633

OTHER PUBLICATIONS

Swain, P. Soya Good; Dominion, Wellington, New Zealand, May 28, 1998, pp. 1-4 from Proquest Direct database.*
A Brief History of Cucumbers; anonymous, URL < http://www.lpl.arizona.edu/~bcohen/cucumbers/history.html> accessed Aug. 11, 2005, citing Swaider et al. and U.P. Hedrick, pp. 1-2.*

* cited by examiner

*Primary Examiner*—Patricia Leith
(74) *Attorney, Agent, or Firm*—Oblon, Spivak, McClelland, Maier & Neustadt, P.C.

(57) ABSTRACT

The present invention is directed to an aromatase activating agent containing a plant selected from among mulberry bark, ginseng, cucumber, and *phellodendron* bark; or *chlorella*; or an extract of any of these ingredients. The aromatase activating agent of the present invention is highly safe to the human body, and useful as a drug or cosmetic composition for prevention, amelioration, or treatment of various lesions caused by estrogen deficiency.

11 Claims, No Drawings

METHOD FOR TREATING LESIONS CAUSED BY ESTROGEN DEFICIENCY WITH EXTRACT OF CUCUMBER

BACKGROUND OF THE INVENTION

1. Field of the Invention

The present invention relates to an aromatase activating agent which augments activity of aromatase, an enzyme which biosynthesizes estrogen from androgen.

2. Background Art

Estrogen represents a class of female hormones which, in humans, are produced primarily in the ovaries. Some known members falling under estrogen are 17β-estradiol, estrone, and estriol.

Estrogen participates in a variety of physiological functions, such as proliferation of the endometrium, and regulation of sexual functions, bone metabolism, and lipid metabolism. Therefore, when the level of estrogen in the body drops with ageing and ovarian functions deteriorate, a variety of pathological conditions are induced, such as menopause symptoms, hypogonadism, autonomic imbalance, lipid metabolism abnormality, vasomotor instability, and osteoporosis.

Meanwhile, estrogen or estrogen-like substances are endocrine disruptors, and therefore, their direct administration is not appropriate for the prevention or amelioration of the above-mentioned symptoms or lesions.

SUMMARY OF THE INVENTION

Accordingly, an object of the present invention is to provide a drug or a cosmetic composition which is useful for the prevention or amelioration, through stimulation of production of estrogen, of a diversity of lesions caused by estrogen deficiency.

Having noted that estrogen is biosynthesized from androgen by the mediation of aromatase, the present inventors have explored natural substances capable of augmenting activities of aromatase, and have found that specific plants and algae possess an aromatase activity-augmenting action.

Thus, the present invention provides an aromatase activating agent containing, as an active ingredient, a plant selected from among mulberry bark, ginseng, cucumber, and *phellodendron* bark; or *chlorella*; or an extract of any of these ingredients.

The present invention also provides use, in production of an aromatase activating agent, of a plant selected from among mulberry bark, ginseng, cucumber, and *phellodendron* bark; or *chlorella*; or an extract of any of these ingredients.

The present invention also provides a method for prevention, amelioration, or treatment of lesions caused by estrogen deficiency, characterized by comprising administering an effective amount of a plant selected from among mulberry bark, ginseng, cucumber, and *phellodendron* bark; or *chlorella*; or an extract of any of these ingredients.

DETAILED DESCRIPTION OF THE INVENTION AND PREFERRED EMBODIMENTS

Among the ingredients of the aromatase activating agent of the present invention, mulberry bark refers to *Morusalba L.* in Moraceae, ginseng refers to *Panax ginseng* C. A. Meyer belonging to the family Araliaceae, cucumber refers to *Cucumis sativus* belonging to the family Cucurbitaceae, and *phellodendron* bark refers to *Phellodendron amurense Ruprecht* belonging to the family Rutaceae. *Chlorella* refers to unicellular green algae which are classified into the genus *Chlorella* belonging to the family Oocystaceae and have a substantially spherical shape of 3 to 10 μm in diameter. No particular limitations are imposed on the species of *chlorella*, and examples of the species of *chlorella* include *Chlorella vulgaris, Chlorella pyrenoidosa*, and *Chlorella regularis*. Of these, *Chlorella vulgaris* is preferred.

Any of the above plants may be used as is. That is, the whole plant, leaves, barks, branches, fruit, or roots may be used without undergoing any treatment. Alternatively, they may be used in a powder form. Preferred portions are the root skin for mulberry bark, the root for ginseng, the immature fruit for cucumber, and the bark for *phellodendron* bark.

When *chlorella* is used, preferably, the whole algae body is employed.

The extracts employed in the present invention encompass the following: extracts obtained through use of any of a variety of solvents, such as those obtained by subjecting the above plants or *chlorella* to extraction procedures at room temperature or under heat, and those obtained through use of Soxhlet extraction apparatus; diluted solutions thereof; concentrates thereof; and dry powder thereof.

Solvents which are employed for yielding plant extracts or *chlorella* extracts may be polar solvents or nonpolar solvents. Examples of such solvents include water; alcohols such as methanol, ethanol, propanol, and butanol, polyhydric alcohols such as propylene glycol and butylene glycol; ketones such as acetone and methyl ethyl ketone; esters such as methyl acetate and ethyl acetate; linear or cyclic ethers such as tetrahydrofuran and diethyl ether; polyethers such as polyethylene glycol; hydrocarbons such as squalane, hexane, cyclohexane, and petroleum ether; aromatic hydrocarbons such as toluene; halogenated hydrocarbons such as dichloromethane, chloroform, and dichloroethane; and carbon dioxide. Any of these may be used in the form of mixture.

Any of the above-mentioned plant extracts or *chlorella* extracts may be used as is. Alternatively, it may be processed into powder or paste after being subjected to dilution, concentration, or freeze-drying.

Also, any of the above-mentioned plant extracts or *chlorella* extracts may be used after it is subjected to a separation technique, such as liquid-liquid partition chromatography, to thereby remove inactive foreign matter from the extracts.

It is also possible that the above-mentioned plants, *chlorella*, and extracts thereof may be used as a mixture of two or more species.

As described in the Examples section hereinbelow, since the mentioned plants and *chlorella*, and the extracts thereof enhance expression of the aromatase gene, it follows that they have a function of activating aromatase. Therefore, when an aromatase activating agent containing as an active agent any of the mentioned plants or *chlorella*, or the extracts thereof is administered to humans as a drug or a cosmetic composition, such an agent will promote production of estrogen in the living body, and thus is expected to provide the following action and effects attributed to estrogen ("Karada no Kagaku" [Science of Human Bodies] No. 219, 2001; Nippon Hyoron-sha).

1) Effects on bone metabolism: The action of parathyroid hormone is suppressed to prevent osteoporosis, through prevention of bone resorption and to promotion of activation of vitamin D in the kidneys.

2) Effects on hyperlipidemia: Prevention of the process in which reduced estrogen concentration promotes LPL (lipoprotein lipase) activity, reducing the number of LDL receptors and causing build-up of blood LDL to thereby result in atherosclerosis. Increase in the expression level of mRNA present in the vascular endothelium, thereby promoting production of NO. Promotion of antioxidation and vasodilation, thereby suppressing arteriosclerosis.

3) Effects on cerebral functions: Improvement of cerebral functions such as those related to memory, cognition, and cerebral blood flow changes, affecting sentiment and emotion. Relationship with depression has also been reported. To Alzheimer's disease in particular, the following has been reported: 1) Acting on neurons, to thereby increase the activity of Ach (acetylcholine) synthase; i.e., choline acetyltransferase, 2) Stimulatiing expression of NGF (nerve growth factor) or BDNF (brain-derived neurotrophic factor) in cholinergic neurons, 3) Synaptic potentiation in the hippocampus, 4) Acting on APP (amyloid precursor protein), to thereby reduce accumulation of β-amyloid and alleviate injury of neurons, and 5) Promoting transportation and utilization of glucose.

4) Effects on menopause symptoms: Relief from hyperactive conditions of the hypothalamus and the pituitary body caused by inactivated negative feedback in the hypothalamus—pituitary body—ovary system, attributed to reduction in estrogen; in other words, alleviation of autonomic imbalance caused by elevated levels of LH (luteinizing hormone) or FSH (follicle stimulating hormone).

5) Effects on eyes: Preventing the onset of macular degeneration and cataract, which are frequently found in menopausal women. In addition, lacrimal gland functions are improved and dry eyes are alleviated.

When the aromatase activating agent of the present invention is used as a drug, the aromatase activating agent may be formed into internal drug preparations such as tablets and capsules, external drug preparations such as ointments, solutions, extracts, lotions, and emulsions, or injections. The drug may contain, in addition to the plants or extracts thereof according to the present invention, one or more pharmacologically acceptable carriers such as auxiliary agents, stabilizers, wetting agents, emulsifiers, absorption enhancers, and surfactants. These carriers may be used in arbitrary combinations.

When the aromatase activating agent of the present invention is used as a cosmetic composition, the composition may take a variety of forms such as water-in-oil emulsions or oil-in-water emulsions, creams, lotions, gels, foams, essences, foundations, packs, sticks, and powders. The cosmetic composition may contain, in addition to any of the plants or plant extracts of the present invention and in arbitrary combinations, one or more additives such as oils, surfactants, ultraviolet absorbers, alcohols, chelating agents, pH regulators, preservatives, thickeners, coloring agents, perfumes, and skin nourishing agents, which are generally used as cosmetic ingredients.

The amount of any of the plants or *chlorella*, or extracts thereof incorporated into the drug or cosmetic composition of the present invention is typically 0.00001 to 1 wt %, preferably 0.0001 to 0.1 wt %, with respect to the entire composition (on a dry basis).

EXAMPLES

The present invention will next be described in detail by way of examples.

Production Example 1

Production of Mulberry Bark Extract

Mulberry bark (10 g) was subjected to extraction with an aqueous ethanol solution (50 v/v %, 25 mL) for about seven days at room temperature, followed by filtration, to thereby yield a mulberry bark extract (yield: 11 mL, evaporation residue: 11.6 w/v %).

Production Example 2

Extracts of the plants and *chlorella* listed in Table 1 below were prepared in accordance with the process of Production Example 1.

TABLE 1

| Plant | Portion subjected to extraction | Solvent employed for extraction |
|---|---|---|
| Ginseng | Root | 90% Ethanol |
| Cucumber | Immature fruit | 40% 1,3-Butanediol |
| Phellodendron bark | Bark | 50% Ethanol |
| Chlorella | Whole algae | Water |

Referential Example 1

Construction of Reporter Gene Assay System

Genomic DNA was extracted from a human normal keratinocyte sample. A DNA fragment in the genomic DNA, the fragment containing a transcriptional control region of human aromatase gene exon 1c and a portion of the exon 1c, was amplified through PCR by use of the following primers.

```
upper primer
5'-GACTAGTAAACAACCACAAAACTGCTC-3'    (SEQ ID NO: 1)
lower primer
5'-AACTGCAGACAAGTCAAAACAAGGAAGC-3'   (SEQ ID NO: 2)
```

The PCR product was treated with restriction enzymes SpeI and PstI, and the product was transferred into a SeaPansy null control vector (TOYO INK MFG. CO., LTD.) at SpeI and PstI sites thereof. The product was used as an Ex1c-luc plasmid in the luciferase assay described below.

Example 1

Effect of Enhanced Expression of Aromatase Gene Exon 1c (1) Materials and Methods (i) Cells Used in Test Immortalized cells derived from keratinocytes (HaCaT cells)

(ii) Plasmid Used in Test

Ex1c-luc (obtained through incorporation of a transcriptional control region of aromatase gene exon 1c (about 1 kb) into luciferase gene on the upstream side thereof)

(iii) Transfection to Cells

HaCaT cells were multiplied in 100-mm dishes until the cells reached subconfluency. Ex1c-luc was introduced into the cells through use of a lipofectamine reagent (Invitrogen). The introduction was performed in accordance with the manufacturer's instructions for the reagent. The amount of the DNA was 8 μg per dish. A DNA-free dish was prepared and subjected to similar procedures.

(iv) Luciferase Assay

The transfected cells were cultured overnight, and the resultant cells were added to wells of a 96-well cell culture plate (about 30,000 cells per well). The volume of the culture broth in each well was 200 μL. On the following day, the plant or *chlorella* extracts prepared in Production Examples 1 and 2 were added to the wells (1% and 0.1%), and the mixtures were cultured for 20 hours. Alamar Blue (BIOSOURCE, 20 μL) was added to each well, followed by incubation for two hours. Fluorescence intensity (excitation light: 544 nm, fluorescence: 590 nm) was measured. Furthermore, luciferase activity was measured through use of a PicaGene Dual SeaPansy luminescence kit (NIPPON GENE). Cell lysis was caused by addition of a cell lysis solution (1×) (25 μL per well), which had been prepared from a 5× cell lysis solution.

(2) Results

The results are shown in Table 2 below.

TABLE 2

|  | Luciferase | Alamar Blue |
| --- | --- | --- |
| Mulberry bark | 118.8% | 154.0% |
| Ginseng | 227.0% | 110.4% |
| Cucumber | 119.0% | 81.7% |
| Phellodendron bark | 116.1% | 100.2% |
| Chlorella | 124.2% | 85.5% |

As is clear from Table 2, each of the extracts exhibits an ability to activate expression of aromatase. Particularly, as compared with the control, ginseng was found to exhibit twice or more the activity.

As described above, the aromatase activating agent of the present invention promotes production of estrogen in the body and has high safety to humans. Therefore, the agent is useful as a drug or cosmetic composition for prevention, amelioration, or treatment of various pathologic conditions caused by estrogen deficiency.

What is claimed is:

1. A method of ameliorating, or treating lesions caused by estrogen deficiency in a subject in need thereof comprising contacting the skin of said subject with a cosmetic composition comprising an effective amount of an alcohol extract of cucumber.

2. The method of claim 1, wherein said alcohol extract of cucumber is an alcohol extract of the immature fruit of cucumber.

3. The method of claim 1, wherein said alcohol extract of cucumber is an alcohol extract of the immature fruit of cucumber and wherein the alcohol used for extraction is 1,3-butanediol.

4. The method of claim 1, wherein the total content of said alcohol extract of cucumber with respect to the entire composition on a dry weight basis ranges from 0.00001 to 1%.

5. The method of claim 1, wherein the total content of said alcohol extract of cucumber with respect to the entire composition on a dry weight basis ranges from 0.0001 to 0.1%.

6. The method of claim 1, wherein said subject in need thereof is a human suffering from menopause.

7. A method of ameliorating, or treating lesions caused by estrogen deficiency in a subject in need thereof comprising administering to said subject an internal drug composition comprising an effective amount of an alcohol extract of cucumber.

8. The method of claim 7, wherein said alcohol extract of cucumber is an alcohol extract of the immature fruit of cucumber and wherein the alcohol used for extraction is 1,3-butanediol.

9. The method of claim 7, wherein the total content of said alcohol extract of cucumber with respect to the entire composition on a dry weight basis ranges from 0.00001 to 1%.

10. The method of claim 7, wherein the total content of said alcohol extract of cucumber with respect to the entire composition on a dry weight basis ranges from 0.0001 to 0.1%.

11. The method of claim 7, wherein said subject in need thereof is a human suffering from menopause.

* * * * *

SEQUENCE LISTING

```
<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Synthetic DNA

<400> SEQUENCE: 1
gactagtaaa caaccacaaa actgctc                                        27

<210> SEQ ID NO 2
<211> LENGTH: 28
<212> TYPE: DNA
<213> ORGANISM: Artificial Sequence
<220> FEATURE:
<223> OTHER INFORMATION: Synthetic DNA

<400> SEQUENCE: 2
aactgcagac aagtcaaaac aaggaagc                                       28
```